US008524483B2

(12) United States Patent
Iida (10) Patent No.: US 8,524,483 B2
(45) Date of Patent: Sep. 3, 2013

(54) GENE INVOLVED IN QUORUM-SENSING SYSTEM OF ACETIC ACID BACTERIUM, ACETIC ACID BACTERIUM BRED BY MODIFICATION OF THE GENE AND METHOD FOR PRODUCTION OF VINEGAR BY USING THE ACETIC ACID BACTERIUM

(75) Inventor: Aya Iida, Handa (JP)

(73) Assignee: Mizkan Group Corporation, Aichi (JP)

( * ) Notice: Subject to any disclaimer, the term of this patent is extended or adjusted under 35 U.S.C. 154(b) by 592 days.

(21) Appl. No.: 12/528,066

(22) PCT Filed: Jan. 18, 2008

(86) PCT No.: PCT/JP2008/000049
§ 371 (c)(1),
(2), (4) Date: Jan. 12, 2010

(87) PCT Pub. No.: WO2008/102519
PCT Pub. Date: Aug. 28, 2008

(65) Prior Publication Data
US 2010/0137641 A1 Jun. 3, 2010

(30) Foreign Application Priority Data
Feb. 23, 2007 (JP) .................................. 2007-043635

(51) Int. Cl.
| | | |
|---|---|---|
| C12N 1/12 | (2006.01) |
| C12N 15/00 | (2006.01) |
| C12N 9/00 | (2006.01) |
| C12N 9/10 | (2006.01) |
| C12Q 1/68 | (2006.01) |
| C07H 21/04 | (2006.01) |

(52) U.S. Cl.
USPC ......... 435/252.1; 435/6.1; 435/440; 435/183; 435/193; 435/320.1; 536/23.2

(58) Field of Classification Search
None
See application file for complete search history.

(56) References Cited

FOREIGN PATENT DOCUMENTS
| | | |
|---|---|---|
| JP | 02002364 | 1/1990 |
| JP | 03219878 | 9/1991 |
| JP | 2003289867 | 10/2003 |
| JP | 2006230329 A | 9/2006 |

OTHER PUBLICATIONS

Q9KJ70. TrEMBLrel Database. 2000.*
Q9KJ71. TrEMBLrel Database. 2000.*
Iida et al. Control of Acetic Acid Fermentation by Quorum Sensing via N-Acylhomoserine Lactones in Gluconacetobacter intermedius. J Bacteriol. Apr. 2008; 190(7): 2546-2555. Published online Feb. 1, 2008.*
Camilli, et al., "Bacterial Small-Molecule Signaling Pathways", Science, (2006), 1113-1116, 311.
Fukushima, Jun, "*Pseudomonas aeruginosa* no Byogensei Hatsugen to Quorum Sensing System", Bioscience & Industry, (2002), 219-224, 60(4).
Iida, et al., "Sakusankin Gluconacetobacter Intermedius ni Okeru Quorum Sensing System no Kaiseki", Japan Society for Bioscience, Biotechnology, and Agrochemistry Taikai Koen Yoshishu, (2007), 175, 2007.
Luo, et al., "In Situ Activation of the Quorum-Sensing Transcription Factor TraR by Cognate and Noncognate Acyl-Homoserine Lactone Ligands: Kinetics and Consequences", Journal of Bacteriology, (2003), 5665-5672, 185(19).
Vial, et al., "N-acyl-homoserine lactone-mediated quorum-sensing in Azospirillum: an exception rather than a rule", FEMS Microbiology Ecology, (2006), 155-168, 58(2).
Fukaya, M., et al., "Improved Transformation Method for Acetobacter with Plasmid DNA," Agric. Bio. Chem (1985) 49:2091-2097.
Lou, Z-Q, et al., "In Situ Activation of the Quorum-Sensing Transcription Factor TraR by Cognate and Noncognate Acyl-Homoserine Lactone Ligands: Kinetics and Consequences," Journal of Bacteriology (2001) 44:239-251.
Ravn, L., et al., "Methods for detecting acylated homoserine lactones produced by Gram-negative bacteria and their application in studies of AHL-production kinetics," Journal of Microbiological Methods (2001) 44:239-251.
Tayama, K., et al., "Transormation of Acetobacter polyoxogenes with Plasmid DNA by Electroporation," Biosci. Biotech. Biochem. (1994) 58:974-975.
Wong, H.C., et al., "Genetic organization of the cellulose synthase operon in Acetobacter xylinum," Proc. Natl. Acad. Sci. (1990) 87:8130-8134.
Bioscience and Industry (2002) 60(4):219-224.
Database UniProtKB/TrEMBL [online] , Accessin No. A1TTR8, <http://srs.ebi.ac.uk/srsbin/cgi-bin/wgetz?-e+[UNIPROT-acc:A1TTR8]+-Vn+2+22 06-FEB-2007 uploaded, [retrieved on Feb. 1, 2008], Feb. 6, 2007.
Database UniProtKB/TrEMBL [online] , Accessin No. Q13HW9, <http://srs.ebi.ac.uk/srsbin/ cgi-bin/wgetz?-e+[UNIPROT-acc:Q13HW9]+-Vn+2> Aug. 22, 2006 uploaded, [retrieved on Feb. 1, 2008], Aug. 22, 2006.

* cited by examiner

*Primary Examiner* — Yong Pak
(74) *Attorney, Agent, or Firm* — Chainey P. Singleton; Edwin S. Flores; Chalker Flores, LLP (57) ABSTRACT

The object of the present invention is to provide a method for efficiently producing vinegar that contains a higher concentration of acetic acid, wherein a gene involved in the acetic acid fermentation ability is obtained, the acetic acid fermentation ability of an acetic acid bacterium is improved by reducing or deleting the function of the protein encoded by the gene. An acetic acid bacterium with a remarkably improved acetic acid fermentation ability was obtained by obtaining genes encoding an acyl homoserine lactone synthase and an acyl homoserine lactone receptor-type transcription factor that are involved in the quorum-sensing system in the acetic acid bacterium, and modifying the genes so as to reduce or delete the function of the quorum-sensing system. Further provided is a method for more efficiently producing vinegar containing a higher concentration of acetic acid by using the acetic acid bacterium.

5 Claims, 4 Drawing Sheets

Fig. 2

| | |
|---|---|
| CTGCAGCCAGCGTCATCGGCTTGGTTGCTATTGTCCTGAACGGTTTATTTAAAGTCAAAA | 60 |
| AAGAAGAAGAAAAAGCTAAAGAAAAAGAAGGCGATAATAAGTCAGCCTAGATAGCCACCA | 120 |
| CTGCGACAATGCGCGAACGGAAATAGCTTTAAGGGCGTCTCGGAAATCATGCGCCTAACC | 180 |
| ACCCTCGCCCTACTCACCACCCCAGCAGCAGCTCACGCCTACGCACCCCGGCACGCCTAT | 240 |
| ACGCCAACCAGCGGCCAAGCTGAGCCAGTCTGCCCCAAGGGCGACCAGCCGGTTTGGGTG | 300 |
| AACACCCGGTCTAGCGTCTACCACTACCGGCACGAACGCTGGTACGGGAACACAAAATAT | 360 |
| GGGCAGTATGAGTGTGAGAAGGACGCGCAGGCCGAGGGGAACAGGCCTACGCGGAATGGC | 420 |
| CAGTAAGAACGGTCAGAACGGGTTTTCTACGTTATCCGCGGGTTTCGCGTCATCAACCTG | 480 |
| AGCCTTGATGCTATGAGAGGCATCTGTGGGTGTGGTCTTCCGTAGATTACGTGACTTATG | 540 |
| GCGCACGCCTCGAACGCCTGACTTCTTGTCCCCCCTTCCGCAATAGCCTGCCTCTCGCAT | 600 |
| TCATAGACGCCGTGTTTGGTTCGGCCATACCAGCGATCGCCCGGCAGATGATAGACGCCA | 660 |
| GTGTTCTGGTTGACCCAGACCATGGTATCAGCAGGGCATGATGGGTGGGGCAGATTTTCG | 720 |
| GCTGCGTAGGCTGCTCCCGGCATGAGGACGGCGATCGCCACCATAAATCTATAGAATAAA | 780 |
| TATATCATATAATTTAGGCTTATTATTGAATGCACTGGAGGTAGATGCGGCATAGATGGT | 840 |
| GGGCTTGACGATTGACCTTCTGGCGAAACTACATGACCTTGAGAACGCAGCCACTAAACA | 900 |
| CGATCTGCTATCCATCTATCTTGATGCCGTCCTGTCAGTCGGGAACGTCCACGTAACCAT | 960 |
| TGTGGAATTGAACAGGATTGAAGACCCTAAAGAAAATTTTATACACGTTGGATATCCGAC | 1020 |
| GGAATGGGTCAATTTCTATATTGAGAACAATTACATAGTCTCTGACCCAATAATAAAAAA | 1080 |
| ATCCAGATTCATGAGCCACCCATATTTCTGGCATGAAATCAAGAACATCAACAAAGCCGA | 1140 |
| AAAAAAGATAATCAGGGACGTATCTGAATTTGGCATAAAAAAGGGGCTGACAATACCGGT | 1200 |
| CCATACGCATGACAGGGTAATTTACGCCATTTGTTTTGCATTTACAGATAAAAACATAGA | 1260 |
| TCGGGAAATTGAGCTTTATTTGCGCGCCTTATCCAATTTCTTCATTACCGGTTATAAAAA | 1320 |
| ATTGGATGAACCGGCGGATATGTCGCTCCCCATTCTTACCCCTCGTGAAAAAGAATGCCT | 1380 |
| GACATGGACAGCCAAGGGCAAAAGCTCATGGGAAACCGGGATGATTGTTGGTGTCAGTGA | 1440 |
| GCGCACAGTTAACTTTCACATCAACAATGCCTTGCTGAAGCTGAAATGTACGAATCGTAT | 1500 |
| CATGGGTGTGGTGCGGGCTATCTGCGCAGGGCTGATTGAACTGTAAAACCTGTCAGGTCT | 1560 |
| GACAGGTAACCTGACCGTCGATTTTCATGAATGATCCTCTCATCCAACAGGAAGAGAGTA | 1620 |
| GATCCATGATCGAAGTCGTAACCGTTGAAAACGCCCACTGGGCCGGAACTGCTCTCGCAG | 1680 |
| AGCAGTTCAAGTTCCGTTACCGCCATTTTGTGGCTAATGAGCAGTGGGAAGTCCCCTTCT | 1740 |
| ACAAGGGCATGGAATACGATCAGTTCGATACGCCTGCTGCTGTCTACCTCGTGTGGCGCG | 1800 |
| ATGTTGCGGGCGTTGTTCGGGGCATGATCCGTCTGCTGCCAACGAACCGGCCTTACATGC | 1860 |
| TGGAAACACTCTGGCCCGATATGATGCCCGATCCGATTGTTCCATCTGGTCCTGCGGTCT | 1920 |
| GGGAAATCACCCGGTTTGGCGTTGAGCGCAATCTGTCCCTATCCCTCCGCAAGCAGATAT | 1980 |
| CAGCCGAACTGATCCTGGCATGCATCGAATTTTCAGTGCTGAATGACATTCACACCTATC | 2040 |
| TGTTTCTGACAGCGTGGGGTGTTCTCAAGCGGATTGTGCCCGGCGCTGGCGTGGAGGCAC | 2100 |
| AGATTCACAGCAGGAAGACACTGCCTTCCGGACATGATGTCGCTTCTGCCGTTGTGCCCG | 2160 |
| TTTCCCAGGCCGTTCTGGATAAGGCCCGAGCCAAGCTGAATATTCATTACGCCGTTCTCG | 2220 |
| ATAACAATAGCATTGAGCAGCAGCATGCAGCATAGGCAGCAGAACGAAGACATGGAAAAA | 2280 |
| AAAGCAGAAAACATCAAAAGCGCATTATCGTTCTTGCGGTCAGAAGCAAGAAA | 2333 |

Fig. 3

MetAsnAspProLeuIleGlnGlnGluGlu SerArgSerMetIleGluValValThrVal
GluAsnAlaHisTrpAlaGlyThrAlaLeu AlaGluGlnPheLysPheArgTyrArgHis
PheValAlaAsnGluGlnTrpGluValPro PheTyrLysGlyMetGluTyrAspGlnPhe
AspThrProAlaAlaValTyrLeuValTrp ArgAspValAlaGlyValValArgGlyMet
IleArgLeuLeuProThrAsnArgProTyr MetLeuGluThrLeuTrpProAspMetMet
ProAspProIleValProSerGlyProAla ValTrpGluIleThrArgPheGlyValGlu
ArgAsnLeuSerLeuSerLeuArgLysGln IleSerAlaGluLeuIleLeuAlaCysIle
GluPheSerValLeuAsnAspIleHisThr TyrLeuPheLeuThrAlaTrpGlyValLeu
LysArgIleValProGlyAlaGlyValGlu AlaGlnIleHisSerArgLysThrLeuPro
SerGlyHisAspValAlaSerAlaValVal ProValSerGlnAlaValLeuAspLysAla
ArgAlaLysLeuAsnIleHisTyrAlaVal LeuAspAsnAsnSerIleGluGlnGlnHis
AlaAla

Fig. 4

MetValGlyLeuThrIleAspLeuLeuAla LysLeuHisAspLeuGluAsnAlaAlaThr
LysHisAspLeuLeuSerIleTyrLeuAsp AlaValLeuSerValGlyAsnValHisVal
ThrIleValGluLeuAsnArgIleGluAsp ProLysGluAsnPheIleHisValGlyTyr
ProThrGluTrpValAsnPheTyrIleGlu AsnAsnTyrIleValSerAspProIleIle
LysLysSerArgPheMetSerHisProTyr PheTrpHisGluIleLysAsnIleAsnLys
AlaGluLysLysIleIleArgAspValSer GluPheGlyIleLysLysGlyLeuThrIle
ProValHisThrHisAspArgValIleTyr AlaIleCysPheAlaPheThrAspLysAsn
IleAspArgGluIleGluLeuTyrLeuArg AlaLeuSerAsnPhePheIleThrGlyTyr
LysLysLeuAspGluProAlaAspMetSer LeuProIleLeuThrProArgGluLysGlu
CysLeuThrTrpThrXaaLysGlyLysSer SerTrpGluThrGlyMetIleValGlyVal
SerGluXaaThrValAsnPheHisIleAsn AsnAlaLeuLeuLysLeuLysCysThrAsn
ArgIleMetGlyValValArgAlaIleCys AlaGlyLeuIleGluLeu

Fig. 5

5'-CCGGAATTCGGATATGTCGCTCCCATTC-3'

Fig. 6

5'-CGGGGTACCGCCAGAGTGTTTCCAGCATG-3'

Fig. 7

5'-CCCAAGCTTCCGATATGATGCCCGATCCG-3'

Fig. 8

5'-CCCAAGCTTCTGCGATGGAGAGCGAGTTC-3'

Fig. 9

5'-CCGCCCGGGAAGCTTCACGCTGCCGCAAG-3'

Fig. 10

5'-GAGCCCGGGGTGGGCGAAGA-3'

Fig. 11

5'-CCGGAATTCTCCGCAATAGCCTGCCTCTC-3'

Fig. 12

5'-CTATCAGATCTACTCTTCCTGTTGG-3'

GENE INVOLVED IN QUORUM-SENSING SYSTEM OF ACETIC ACID BACTERIUM, ACETIC ACID BACTERIUM BRED BY MODIFICATION OF THE GENE AND METHOD FOR PRODUCTION OF VINEGAR BY USING THE ACETIC ACID BACTERIUM

CROSS-REFERENCE TO RELATED APPLICATIONS

This application is a 35 U.S.C. §371 national filing in the United States and claims priority to Japanese Patent Application Serial No. 2007-043635, filed Feb. 23, 2007, and PCT Application Serial No. PCT/JP2008/000049, filed Jan. 18, 2008, the entire contents of which are incorporated herein by reference.

TECHNICAL FIELD

The present invention relates to genes involved in the quorum-sensing system in an acetic acid bacterium, an acetic acid bacterium wherein its ability of acetic acid fermentation (hereinafter may be referred to as an acetic acid fermentation ability) without decreasing the growth ability and the acetic acid formation ability even at a higher acetic acid concentration is enhanced by reducing or deleting the function of one or more proteins encoded by these genes involved in the quorum-sensing system, a method for producing vinegar using the acetic acid bacterium, and vinegar produced by the production method.

BACKGROUND ART

Acetic acid bacteria are microorganisms widely used in the vinegar production. Especially, acetic acid bacteria belonging to the genus *Acetobacter* or the genus *Gluconacetobacter* are utilized in the industrial acetic acid fermentation.

In the acetic acid fermentation, ethanol in the medium is oxidized and converted to acetic acid by acetic acid bacteria, and consequently, acetic acid is accumulated in the medium. However, since acetic acid is also inhibitory to acetic acid bacteria, the growth ability and acetic acid formation ability of acetic acid bacteria gradually decrease as the acetic acid concentration in the medium is raised due to the increase in the accumulation amount of acetic acid.

Accordingly, it has been desired to develop an acetic acid bacterium which is capable of fermenting acetic acid without decreasing the growth ability or acetic acid formation ability even at a higher acetic acid concentration, in other words, an acetic acid bacterium having a better acetic acid fermentation ability.

Many attempts are disclosed as an attempt to develop such acetic acid bacterium having an improved acetic acid fermentation ability. Examples of such attempts include: a transformant wherein three genes (aarA, aarB, aarC) contained in a gene cluster derived from an acetic acid bacterium are amplified, where these three genes are capable of restoring the acetic acid sensitive mutants of the acetic acid bacterium belonging to the genus *Acetobacter* to its original state (see for example, Patent document 1); an example in which a gene encoding a membrane-binding aldehyde dehydrogenase (ALDH) cloned from an acetic acid bacterium is introduced into an acetic acid bacterium (see for example, Patent document 2); and an example in which aconitase gene derived from an acetic acid bacterium is overexpressed (see for example, Patent document 3).

Actually, however, none of the attempts has succeeded in conferring a sufficient acetic acid fermentation ability. Therefore, it has been desired to obtain an acetic acid bacterium in which the acetic acid fermentation ability is enhanced and which is capable of more efficiently producing vinegar containing a high concentration of acetic acid.

On the other hand, the presence of an intercellular signal communication system in which transcription of specific genes is controlled depending on the cell density has been recently elucidated in many bacteria. This system is called quorum-sensing system (a control system sensing a cell density) and is involved in the expression control for various functions such as bioluminescence, exoenzyme production, toxic virulence, biofilm formation, and antibiotic production.

Two kinds of proteins are involved in the quorum-sensing system which has been found in many Gram negative bacteria such as *Vibrio fischeri* (see for example, Non-Patent document 1). The proteins are an acyl homoserine lactone synthase that synthesizes acyl homoserine lactone which is an intracellular signal molecule, and an acyl homoserine lactone receptor-type transcription factor that is a receptor of acyl homoserine lactone and that also functions as a transcription factor. Acyl homoserine lactone produced by an acyl homoserine lactone synthase in a bacterial cell diffuses inside and outside the bacterial cell. As the concentration of acyl homoserine lactone is increased, it forms a complex with the acyl homoserine lactone receptor-type transcription factor in a bacterial cell to control the gene transcription.

In spite that the quorum-sensing system has an important function as described above, no analysis on the quorum-sensing system in acetic acid bacteria has been carried out at all and its presence and function remained unknown. Further, it has not been conventionally known at all that the quorum-sensing system is involved in the acetic acid fermentation ability.

Patent document 1: Japanese Laid-Open Patent Application No. 3-219878
Patent document 2: Japanese Laid-Open Patent Application No. 2-2364
Patent document 1: Japanese Laid-Open Patent Application No. 2003-289867
Non-patent document 1: Bioscience and Industry, Vol. 60, No. 4, pp. 219-224, 2002

DISCLOSURE OF THE INVENTION

Object to be Solved by the Invention

It is the object of the present invention to provide a method for improving an acetic acid fermentation ability of an acetic acid bacterium by obtaining a gene involved in the acetic acid fermentation ability and then reducing or deleting a function of the protein encoded by the gene, and a method for more efficiently producing vinegar containing a high concentration of acetic acid by using the acetic acid bacterium which is conferred an improved acetic acid fermentation ability by the above-mentioned method. The present invention further provides vinegar produced by the production method.

Means to Solve the Object

The present inventor has made a keen study to solve the above objects, and focused on a gene involved in the quorum-sensing system even under the situation where the presence of the quorum-sensing system in acetic acid bacteria had not yet been known. The present inventor thus conducted various experiments in order to obtain a gene involved in quorum-sensing system of an acetic acid bacterium by the methods including a genomic southern blotting based on conventionally known genes involved in quorum-sensing system or PCR method using degenerate primers prepared based on the sequence information of the known genes, but without success. (The cause for the failure turned out to be the low homology at last upon performing the sequence analysis of genes involved in a quorum-sensing system of an acetic acid bacterium after the cloning.) Therefore, the present inventor started to try a cloning method for genes involved in the quorum-sensing system using a reporter strain as an indicator. Several thousand colonies of a chromosomal DNA library prepared by shotgun cloning were tested using several reporter strains. However, not all of the reporter strains brought success, and cloning of genes involved in a quorum-sensing system did not succeed at first. In an assay in which *Agrobacterium tumefaciens* NTL4 (pZLR4) was selected as a reporter strain after having used the above several reporter strains, cloning of genes involved in the quorum-sensing system of an acetic acid bacterium was at last succeeded after testing several thousand colonies of the chromosomal DNA library prepared by shotgun cloning. In this way, genes encoding two kinds of proteins that are involved in the quorum-sensing system in an acetic acid bacterium, that is, genes encoding an acyl homoserine lactone synthase and an acyl homoserine lactone receptor-type transcription factor were found in an acetic acid bacterium for the first time. The present inventor confirmed that, surprisingly, an acetic acid fermentation ability of an acetic acid bacterium is remarkably enhanced by modifying the genes encoding an acyl homoserine lactone synthase and an acyl homoserine lactone receptor-type transcription factor to reduce or delete the function of these proteins. It was further found out by the present inventor that vinegar containing a high concentration of acetic acid can be more efficiently produced by performing an acetic acid fermentation using the acetic acid bacterium wherein its acetic acid fermentation ability is thus remarkably enhanced. The present invention has thus been completed.

The present invention relates to the following.

(1) A protein shown by following (A), (B) or (C):
(A) a protein consisting of the amino acid sequence shown by SEQ ID NO: 2 in the sequence listing;
(B) a protein which consists of an amino acid sequence wherein one or a few amino acids are substituted, deleted, inserted or added in the amino acid sequence shown by SEQ ID NO: 2 in the sequence listing, and which has the activity of an acyl homoserine lactone synthase;
(C) a protein which consists of an amino acid sequence having at least 85% or more identity to the amino acid sequence shown by SEQ ID NO: 2 in the sequence listing, and which has the activity of an acyl homoserine lactone synthase.

(2) A DNA encoding a protein shown by following (A), (B) or (C):
(A) a protein consisting of the amino acid sequence shown by SEQ ID NO: 2 in the sequence listing;
(B) a protein which consists of an amino acid sequence wherein one or a few amino acids are substituted, deleted, inserted or added in the amino acid sequence shown by SEQ ID NO: 2 in the sequence listing, and which has the activity of an acyl homoserine lactone synthase;
(C) a protein which consists of an amino acid sequence having at least 85% or more identity to the amino acid sequence shown by SEQ ID NO: 2 in the sequence listing, and which has the activity of an acyl homoserine lactone synthase.

(3) A DNA shown by following (A), (B), (C) or (D):
(A) a DNA consisting of the nucleotide sequence of nucleotide numbers 1639 to 2268 in the nucleotide sequence shown by SEQ ID NO: 1 in the sequence listing;
(B) a DNA which hybridizes under stringent conditions to a DNA consisting of a sequence complementary to the nucleotide sequence of nucleotide numbers 1639 to 2268 in the nucleotide sequence shown by SEQ ID NO: 1 in the sequence listing, and which encodes a protein having the activity of an acyl homoserine lactone synthase;
(C) a DNA which hybridizes under stringent conditions to a DNA consisting of a nucleotide sequence produced from a part of the nucleotide sequence of nucleotide numbers 1639 to 2268 in the nucleotide sequence shown by SEQ ID NO: 1 in the sequence listing and having the function as a primer pair or a probe, and which encodes a protein having the activity of an acyl homoserine lactone synthase;
(D) a DNA which consists of a nucleotide sequence wherein one or a few nucleotides are substituted, deleted, inserted or added in the nucleotide sequence of nucleotide numbers 1639 to 2268 in the nucleotide sequence shown by SEQ ID NO: 1 in the sequence listing, and which encodes a protein having the activity of an acyl homoserine lactone synthase.

(4) A protein shown by following (A), (B) or (C):
(A) a protein consisting of the amino acid sequence shown by SEQ ID NO: 3 in the sequence listing;
(B) a protein which consists of an amino acid sequence wherein one or a few amino acids are substituted, deleted, inserted or added in the amino acid sequence shown by SEQ ID NO: 3 in the sequence listing, and which has the function as an acyl homoserine lactone receptor-type transcription factor;
(C) a protein which consists of an amino acid sequence having at least 85% or more identity to the amino acid sequence shown by SEQ ID NO: 3 in the sequence listing, and which has the function as an acyl homoserine lactone receptor-type transcription factor.

(5) A DNA encoding a protein shown by following (A), (B) or (C):
(A) a protein consisting of the amino acid sequence shown by SEQ ID NO: 3 in the sequence listing;
(B) a protein which consists of an amino acid sequence wherein one or a few amino acids are substituted, deleted, inserted or added in the amino acid sequence shown by SEQ ID NO: 3 in the sequence listing, and which has the function as an acyl homoserine lactone receptor-type transcription factor;
(C) a protein which consists of an amino acid sequence having at least 85% or more identity to the amino acid sequence shown by SEQ ID NO: 3 in the sequence listing, and which has the function as an acyl homoserine lactone receptor-type transcription factor.

(6) A DNA shown by following (A), (B), (C) or (D):
(A) a DNA consisting of the nucleotide sequence of nucleotide numbers 849 to 1559 in the nucleotide sequence shown by SEQ ID NO: 1 in the sequence listing;
(B) a DNA which hybridizes under stringent conditions to a DNA consisting of a sequence complementary to the nucleotide sequence of nucleotide numbers 849 to 1559 in the nucleotide sequence shown by SEQ ID NO: 1 in the sequence listing, and which encodes a protein having the function as an acyl homoserine lactone receptor-type transcription factor;
(C) a DNA which hybridizes under stringent conditions to a DNA consisting of a nucleotide sequence produced from a part of the nucleotide sequence of nucleotide numbers 849 to 1559 and having the function as a primer pair or a probe, and which encodes a protein having the function as an acyl homoserine lactone receptor-type transcription factor;

(D) a DNA which consists of a nucleotide sequence wherein one or a few nucleotides are substituted, deleted, inserted or added in the nucleotide sequence of nucleotide numbers 849 to 1559 in the nucleotide sequence shown by SEQ ID NO: 1 in the sequence listing, and which encodes a protein having the function as an acyl homoserine lactone receptor-type transcription factor.

(7) A method for enhancing the acetic acid fermentation ability, wherein the function of one or two proteins which are encoded by the genes involved in the quorum-sensing system in the acetic acid bacterium is reduced or deleted.

(8) A method for enhancing the acetic acid fermentation ability according to the above (7), wherein the gene involved in the quorum-sensing system is a gene of an acyl homoserine lactone synthase or a gene of an acyl homoserine lactone receptor-type transcription factor.

(9) An acetic acid bacterium wherein the acetic acid fermentation ability is enhanced by the method for enhancing the acetic acid fermentation ability according to the above (7) or (8).

(10) A method for producing vinegar, wherein the acetic acid bacterium according to the above (9) is cultured in an alcohol-containing medium and acetic acid is generated and accumulated in the medium.

(11) A vinegar produced by the method according to the above (10).

Effect of the Invention

According to the present invention, genes involved in the quorum-sensing system in an acetic acid bacterium and proteins encoded by the genes can be provided. More specifically, a gene encoding an acyl homoserine lactone synthase of an acetic acid bacterium and said enzyme protein, and a gene encoding an acyl homoserine lactone receptor-type transcription factor and said transcription factor protein and the like are provided. Also provided is a method for remarkably enhancing the acetic acid fermentation ability of an acetic acid bacterium by reducing or deleting the function of the proteins encoded by the genes. Further, a method for more efficiently producing vinegar containing a high concentration of acetic acid by remarkably enhancing the acetic acid fermentation ability is provided, and vinegar containing a high concentration of acetic acid produced by the above production method is also provided.

BRIEF EXPLANATION OF THE DRAWINGS

FIG. 2 shows the nucleotide sequence of a DNA fragment containing the gene of an acyl homoserine lactone synthase and the gene of an acyl homoserine lactone receptor-type transcription factor (SEQ ID NO: 1).

FIG. 3 shows the amino acid sequence of an acyl homoserine lactone synthase (SEQ ID NO: 2).

FIG. 4 shows the amino acid sequence of an acyl homoserine lactone receptor-type transcription factor (SEQ ID NO: 3).

FIG. 5 shows the nucleotide sequence of primer 1 (SEQ ID NO: 4).

FIG. 6 shows the nucleotide sequence of primer 2 (SEQ ID NO: 5).

FIG. 7 shows the nucleotide sequence of primer 3 (SEQ ID NO: 6).

BEST MODE OF CARRYING OUT THE INVENTION

The present invention is explained in detail in the following.

A protein of the present invention is a protein encoded by a gene which is involved in the quorum-sensing system in an acetic acid bacterium. Specifically exemplified are a protein consisting of the amino acid sequence shown by SEQ ID NO: 2 (FIG. 3) in the sequence listing, and a protein which consists of an amino acid sequence wherein one or a few amino acids are substituted, deleted, inserted or added in the amino acid sequence shown by SEQ ID NO: 2 (FIG. 3) in the sequence listing, and which has the activity of an acyl homoserine lactone synthase. It further relates to a protein which consists of an amino acid sequence having at least 85% or more identity to the amino acid sequence shown by SEQ ID NO: 2 (FIG. 3) in the sequence listing, and which has the activity of an acyl homoserine lactone synthase.

A protein of the present invention is further exemplified by a protein consisting of the amino acid sequence shown by SEQ ID NO: 3 (FIG. 4) in the sequence listing, and a protein which consists of an amino acid sequence wherein one or a few amino acids are substituted, deleted, inserted or added in the amino acid sequence shown by SEQ ID NO: 3 (FIG. 4) in the sequence listing, and which has the function as an acyl homoserine lactone receptor-type transcription factor. It further relates to a protein which consists of an amino acid sequence having at least 85% or more identity to the amino acid sequence shown by SEQ ID NO: 3 (FIG. 4) in the sequence listing, and which has the function as an acyl homoserine lactone receptor-type transcription factor.

An acyl homoserine lactone synthase herein refers to a protein that catalyzes biosynthesis of acyl homoserine lactone. In the present invention, "a protein which has the activity of an acyl homoserine lactone synthase" refers to a protein having an enzymatic activity at the level of 20% or more, preferably 50% or more, more preferably 80% or more of the activity of an acyl homoserine lactone synthase of a protein consisting of the amino acid sequence shown by SEQ ID NO: 2 (FIG. 3). Further, an acyl homoserine lactone receptor-type transcription factor refers to a protein having a function that can control gene transcription by forming a complex with acyl homoserine lactone. In the present invention, "a protein which has the function as an acyl homoserine lactone receptor-type transcription factor" refers to a protein having a function at the level of 20% or more, preferably 50% or more, more preferably 80% or more of the function of the protein, consisting of the amino acid sequence shown by SEQ ID NO: 3 (FIG. 4) in the sequence listing, to control transcription of various genes.

The method of obtaining and preparing a protein of the present invention is not particularly limited and the protein may be any of a naturally-occurring protein, chemically synthesized protein, or a recombinant protein prepared by a gene recombination technique. When obtaining a naturally-occurring protein of the present invention, the protein can be obtained from the cells expressing it by appropriately combining isolation and purification methods for proteins.

When preparing a protein of the present invention by chemical synthesis, the protein of the present invention can be synthesized according to a chemical synthesis method such as Fmoc method (fluorenylmethyloxycarbonyl method), tBOC method (t-butyloxycarbonyl method) or the like. A protein of the present invention can also be synthesized by utilizing various commercially-available peptide synthesizers.

Further, when preparing a protein of the present invention by a gene recombination technique, a protein of the present invention can be prepared by introducing a DNA consisting of a nucleotide sequence encoding the protein into a suitable expression system. Among these methods, it is preferred to prepare a protein of the present invention by a gene recombination technique which enables the preparation with a relatively easy operation at a large quantity.

When preparing a protein of the present invention by a gene recombination technique, known methods including anion- or cation-exchange chromatography; phosphocellulose chromatography; hydrophobic interaction chromatography; affinity chromatography; hydroxyapatite chromatography; and lectin chromatography may be employed after performing ammonium sulfate or ethanol precipitation and acid extraction to recover and purify the protein from the cell culture, where a high-speed liquid chromatography is preferably employed.

Particularly, the purified products of these proteins can be obtained with affinity chromatography using a column to which an antibody such as a monoclonal antibody against a protein of the present invention is bound, or a column to which a substance having affinity to the peptide tag is bound when a usual peptide tag has been added to a protein of the present invention.

Further, a protein consisting of an amino acid sequence wherein one or a few amino acids are substituted, deleted, inserted or added in the amino sequence shown by SEQ ID NO: 2 (FIG. 3) or SEQ ID NO: 3 (FIG. 4) in the sequence listing; or a protein consisting of an amino acid sequence having at least 85% or more identity to the amino acid sequence shown by SEQ ID NO: 2 (FIG. 3) or SEQ ID NO: 3 (FIG. 4) in the sequence listing, can be appropriately prepared or obtained by a skilled person in the art based on the nucleotide sequence information shown by SEQ ID NO: 1 (FIG. 2) in the sequence listing which is an example of the nucleotide sequence encoding the amino acid sequence shown by SEQ ID NO: 2 (FIG. 3) or SEQ ID NO: 3 (FIG. 4).

For example, a homologue of the DNA can be isolated from acetic acid bacteria belonging to the genus *Acetobacter* or the genus *Gluconacetobacter*, or from other acetic acid bacteria by carrying out a screening under appropriate conditions by a polymerase chain reaction (PCR reaction) that uses as a primer an oligonucleotide synthesized based on the nucleotide sequence shown by SEQ ID NO: 1 (FIG. 2) in the sequence listing, or by a hybridization using as a probe an oligonucleotide synthesized based on the above nucleotide sequence. The full-length DNA of the homologous DNA is cloned, integrated into an expression vector and expressed in an appropriate host, and the protein encoded by the homologous DNA can be prepared.

An oligonucleotide can be synthesized according to a conventional method using, for example, various commercially-available DNA synthesizers. Further, a PCR reaction can be performed according to a conventional method using a thermal cycler, Gene Amp PCR System 2400 manufactured by Applied Biosystems, with the use of TaqDNA polymerase (Takara Bio Inc.) or KOD-Plus (Toyobo Co., Ltd.).

It is also possible to bind the above protein of the present invention with a marker protein and/or a peptide tag to provide a fusion protein. The marker protein is not particularly limited as long as it is a conventionally known marker protein. Specific examples of the marker protein include enzymes such as alkaline phosphatase and HRP, the Fc region of an antibody, and a fluorescent material such as GFP. Further, specific examples of the peptide tag include conventionally known peptide tags including epitope tags such as HA, FLAG, Myc; and affinity tags such as GST, maltose-binding protein, biotinated peptide, and oligohistidine. The fusion protein can be produced by a common method, and is useful for a purification of a protein of the present invention, a detection of a protein of the present invention and a quantitative determination of an antibody against a protein of the present invention by utilizing affinity between Ni-NTA and His tag. The fusion protein is also useful as a laboratory reagent in the field to which the present invention pertains.

Further, examples of a DNA of the present invention include: a DNA encoding a protein consisting of the amino acid sequence shown by SEQ ID NO: 2 (FIG. 3) in the sequence listing; a DNA encoding a protein which consists of an amino acid sequence wherein one or a few amino acids are substituted, deleted, inserted or added in the amino acid sequence shown by SEQ ID NO: 2 (FIG. 3) in the sequence listing, and which has the activity of an acyl homoserine lactone synthase; a DNA encoding a protein which consists of an amino acid sequence having at least 85% or more identity to the amino acid sequence shown by SEQ ID NO: 2 (FIG. 3) in the sequence listing, and which has the activity of an acyl homoserine lactone synthase; a DNA consisting of the nucleotide sequence of nucleotide numbers 1639 to 2268 in the nucleotide sequence shown by SEQ ID NO: 1 (FIG. 2) in the sequence listing; a DNA which hybridizes under stringent conditions to a DNA consisting of a sequence complementary to the nucleotide sequence of nucleotide numbers 1639 to 2268 in the nucleotide sequence shown by SEQ ID NO: 1 (FIG. 2) in the sequence listing, and which encodes a protein having the activity of an acyl homoserine lactone synthase; a DNA which hybridizes under stringent conditions to a DNA consisting of a nucleotide sequence produced from a part of the nucleotide sequence of nucleotide numbers 1639 to 2268 in the nucleotide sequence shown by SEQ ID NO: 1 (FIG. 2) in the sequence listing and having a function as a primer pair or a probe, and which encodes a protein having the activity of an acyl homoserine lactone synthase; and a DNA which consists of a nucleotide sequence wherein one or a few nucleotides are substituted, deleted, inserted or added in the nucleotide sequence of nucleotide numbers 1639 to 2268 in the nucleotide sequence shown by SEQ ID NO: 1 (FIG. 2) in the sequence listing, and which encodes a protein having the activity of an acyl homoserine lactone synthase.

Further, examples of a DNA of the present invention include: a DNA encoding a protein consisting of the amino acid sequence shown by SEQ ID NO: 3 (FIG. 4) in the sequence listing; a DNA encoding a protein which consists of an amino acid sequence wherein one or a few amino acids are substituted, deleted, inserted or added in the amino acid sequence shown by SEQ ID NO: 3 (FIG. 4) in the sequence listing, and which has the function as an acyl homoserine lactone receptor-type transcription factor; a DNA encoding a protein which consists of an amino acid sequence having at least 85% or more identity to the amino acid sequence shown by SEQ ID NO: 3 (FIG. 4) in the sequence listing, and which has the function as an acyl homoserine lactone receptor-type transcription factor; a DNA consisting of the nucleotide sequence of nucleotide numbers 849 to 1559 in the nucleotide sequence shown by SEQ ID NO: 1 (FIG. 2) in the sequence listing; a DNA which hybridizes under stringent conditions to a DNA consisting of a sequence complementary to the nucleotide sequence of nucleotide numbers 849 to 1559 in the nucleotide sequence shown by SEQ ID NO: 1 (FIG. 2) in the sequence listing, and which encodes a protein having the function as an acyl homoserine lactone receptor-type transcription factor; a DNA which hybridizes under stringent conditions to a DNA consisting of a nucleotide sequence produced from a part of the nucleotide sequence of nucleotide numbers 849 to 1559 in the nucleotide sequence shown by SEQ ID NO: 1 (FIG. 2) in the sequence listing and having a function as a primer pair or a probe, and which encodes a protein having the function as an acyl homoserine lactone receptor-type transcription factor; and a DNA which consists of a nucleotide sequence wherein one or a few nucleotides are substituted, deleted, inserted or added in the nucleotide sequence of nucleotide numbers 849 to 1559 in the nucleotide sequence shown by SEQ ID NO: 1 (FIG. 2) in the sequence listing, and which encodes a protein having the function as an acyl homoserine lactone receptor-type transcription factor.

As above, a DNA encoding a protein having the activity of an acyl homoserine lactone synthase or a protein having the function as an acyl homoserine lactone receptor-type transcription factor may be a DNA that encodes a protein having deletion, substitution, insertion or addition of one or a few amino acids at a single site or plural sites, as long as the function of the encoded protein is not impaired.

A DNA encoding a protein that is substantially the same as a protein having the activity of an acyl homoserine lactone synthase or a protein having the function as an acyl homoserine lactone receptor-type transcription factor can be obtained by alteration of a nucleotide sequence, such modification being a substitution, deletion, insertion, addition, or inversion of an amino acid at a particular site by means of, for example, site-directed mutagenesis. Further, an altered DNA such as the above can also be obtained by a conventionally known mutagenic treatment. Still further, it is possible to obtain a DNA that encodes substantially the same protein from acetic acid bacteria in general, or from species, strains, mutants, or variants of the genus *Acetobacter* or the genus *Gluconacetobacter*, in particular, because it is generally known that an amino acid sequence of a protein and a nucleotide sequence encoding the same are slightly different among the species, strains, mutants or variants.

The above "amino acid sequence wherein one or a few amino acids are substituted, deleted, inserted or added" means, for example, an amino acid sequence wherein any number of amino acids, for example, 1 to 20, preferably 1 to 15, more preferably 1 to 10, and still more preferably 1 to 5 amino acids, are substituted, deleted, inserted or added. Further, the above "nucleotide sequence wherein one or a few nucleotides are substituted, deleted, inserted or added" means, for example, a nucleotide sequence wherein any number of nucleotides, for example, 1 to 20, preferably 1 to 15, more preferably 1 to 10, and still more preferably 1 to 5 nucleotides are substituted, deleted, inserted or added.

For example, these DNAs consisting of a nucleotide sequence comprising a substitution, deletion, insertion, or addition of one or a few nucleotides (mutated DNAs) can also be prepared by any method known to a skilled person in the art, such as chemical synthesis, genetic engineering technique, and mutagenesis, as stated above. Specifically, mutated DNAs can be obtained by introducing a mutation into the DNA consisting of the nucleotide sequence shown by SEQ ID NO: 1 in the sequence listing, using a method of allowing a mutagenic agent to contact with and act on the DNA; a method of irradiating the DNA with ultraviolet; a genetic engineering technique or the like. The site-directed mutagenesis, one of the genetic engineering techniques, is useful as it is a technique that allows an introduction of a specific mutation into a specific site, and can be performed according to the method described in Molecular Cloning: A laboratory Manual, 2nd Ed., Cold Spring Harbor Laboratory, Cold Spring Harbor, N.Y., 1989, or in Current Protocols in Molecular Biology, Supplement 1-38, John Wiley & Sons (1987-1997), or the like. An expression of this mutated DNA using an appropriate expression system provides a protein consisting of an amino acid sequence comprising a substitution, deletion, insertion or addition of one or a few amino acids.

The above "amino acid sequence having at least 85% or more identity to the amino acid sequence shown by SEQ ID NO: 2 (FIG. 3) or SEQ ID NO: 3 (FIG. 4) in the sequence listing" is not particularly limited as long as the identity to the amino acid sequence shown by SEQ ID NO: 2 (FIG. 3) or SEQ ID NO: 3 (FIG. 4) in the sequence listing is 85% or more. This means that the identity is, for example, 85% or more, preferably 90% or more, more preferably 95% or more, and particularly preferably 98% or more.

The above "under stringent conditions" refers to a condition under which a so-called specific hybrid is formed while a non-specific hybrid is not formed. Specific examples include a condition under which DNAs sharing 50% or more, preferably 70% or more identity hybridize each other, while DNAs with the lower identity do not hybridize; or a hybridization condition at a salt concentration corresponding to 1×SSC, 0.1% SDS, or 0.1×SSC, 0.1% SDS at 65° C., which is a washing condition for a usual southern hybridization.

Further, the above "DNA that hybridizes under stringent conditions" means a DNA that can be obtained by using a method such as a colony hybridization, plaque hybridization or southern-blot hybridization using nucleic acids such as DNA or RNA as a probe. Specifically exemplified is a DNA that can be identified by conducting a hybridization at 65° C. in the presence of 0.7 to 1.0 M NaCl using a filter on which a colony- or plaque-derived DNA or a fragment thereof is immobilized, and washing the filter under the condition of 65° C. with about 0.1 to 2-fold-concentration SSC solution (the composition of the one-fold-concentration SSC solution is: 150 mM sodium chloride and 15 mM sodium citrate).

Hybridization can be performed according to the method described in Molecular Cloning: A laboratory Manual, 2nd Ed., Cold Spring Harbor Laboratory, Cold Spring Harbor, N.Y., 1989 or the like. Examples of a DNA that can hybridize under stringent conditions include a DNA having an identity above a certain level to a nucleotide sequence of a DNA used as a probe. A DNA having an identity of, for example, 60% or more, preferably 70% or more, more preferably 80% or more, still more preferably 90% or more, particularly preferably 95% or more, and most preferably 98% or more, can be exemplified advantageously.

A method of obtaining or preparing a DNA of the present invention is not particularly limited. The DNA of interest can be isolated by preparing an appropriate probe or primer based on the nucleotide sequence information shown by SEQ ID NO: 1 (FIG. 2) or the amino acid sequence information shown by SEQ ID NO: 2 (FIG. 3) in the sequence listing or SEQ ID NO: 3 (FIG. 4) in the sequence listing disclosed herein, and using the probe or primer for screening a cDNA library where the DNA is expected to exist, or the DNA can be prepared by chemical synthesis according to a common method.

A genomic DNA of the present invention can be obtained, for example, by preparing a cDNA library according to a common method from acetic acid bacteria belonging to the genus *Acetobacter* or the genus *Gluconacetobacter*, and then selecting from this library a desired clone using an appropriate probe which is specific to the genomic DNA of the present invention. Further, isolation of total RNA, isolation and purification of mRNAs, acquisition and cloning of cDNAs and the like from these acetic acid bacteria can all be performed according to a common method. Examples of the method of screening a genomic DNA of the present invention from a cDNA library include the methods commonly used by a skilled person in the art such as a method described in Molecular Cloning, 2nd ed.

Specifically, a DNA of the present invention can be obtained from the chromosomal DNA of *Gluconacetobacter intermedius* NCI 1051 by the following steps.

The chromosomal DNA can be obtained by a common method disclosed (see for example, Japanese Laid-Open Patent Application No. 60-9489). A chromosomal DNA library is prepared in order to isolate a gene encoding an acyl homoserine lactone synthase from the obtained chromosomal DNA. First, the chromosomal DNA is partially fragmented with an appropriate restriction enzyme to obtain a mixture of various DNA fragments. A wide variety of restriction enzymes can be used by adjusting the cleavage degree through adjustment of the cleavage reaction time and the like. For example, PstI is allowed to act on and digest the chromosomal DNA at the temperature of 30° C. or above, preferably at 37° C., at an enzyme concentration of 1-10 units/ml for various durations (1 minute to 2 hours).

Next, the cleaved chromosomal DNAs are ligated to a vector DNA which is replicable autonomously in *Escherichia coli* and which has an antibiotic-resistant marker gene, to produce a recombinant DNAs.

Specifically, the restriction enzyme PstI used for cleaving the chromosomal DNA is allowed to act on the vector DNA for 1 hour or more under the condition of a temperature of 37° C. and an enzyme concentration of 1-100 units/ml to completely digest and cleave the vector DNA. Then the mixture of chromosomal DNA fragments is mixed with the digested and cleaved vector DNA. T4 DNA ligase is allowed to act on this mixture under the condition of a temperature of 4 to 16° C. and an enzyme concentration of 1-100 units/ml for 1 hour or more, preferably for 6 to 24 hours to obtain recombinant DNAs.

*Escherichia coli* is transformed by using thus obtained recombinant DNAs. Transformants are selected on a LB agar medium supplemented with an antibiotic corresponding to the antibiotic-resistant gene contained in the vector. $10^3$ to $10^5$ antibiotic-resistant transformants grown on the above selection medium are obtained, and are used as a chromosomal DNA library.

A strain having a fragment comprising a gene encoding an acyl homoserine lactone synthase is selected from the above chromosomal DNA library according to the following method. Specifically, onto a medium inoculated with a reporter strain that produces a pigment in the presence of acyl homoserine lactone (see for example, Journal of Microbiological Methods, Vol. 44, pp. 239-251, 2001), strains from the chromosomal DNA library are inoculated. Then a strain by which a pigment production is induced in the reporter strain is selected. A plasmid is recovered from thus selected strain so that a gene encoding an acyl homoserine lactone synthase can be obtained.

Since a gene encoding an acyl homoserine lactone receptor-type transcription factor is, in many cases, present adjacent to a gene encoding an acyl homoserine lactone synthase, a gene encoding an acyl homoserine lactone receptor-type transcription factor can be obtained by the following method.

Briefly, a gene encoding an acyl homoserine lactone receptor-type transcription factor can be obtained by determining the upstream and downstream nucleotide sequences of a gene encoding an acyl homoserine lactone synthase obtained as described above, and carrying out a motif search using a homology search by DDBJ/EMBL/Genbank and SWISS-PROT/PIR as well as a NCBI domain search (http://www.ncbi.nlm.nih.gov/structure/cdd/cdd.shtml). When the upstream and downstream nucleotide sequences of a gene encoding an acyl homoserine lactone synthase are short, the upstream and downstream nucleotide sequences with sufficient length may be obtained by hybridization using probes prepared based on those short sequences.

Since the nucleotide sequence of a DNA of the present invention has been elucidated, the DNA can also be obtained by a polymerase chain reaction (PCR reaction) using the genomic DNA of *Gluconacetobacter intermedius* as a template and an oligonucleotide synthesized based on the nucleotide sequence as a primer, or it can be obtained by hybridization using an oligonucleotide synthesized based on the nucleotide sequence as a probe. A chromosomal DNA can be obtained by a common method disclosed (see for example, Japanese Laid-Open Patent Application No. 60-9489).

An oligonucleotide can be synthesized according to a common method using, for example, various commercially-available DNA synthesizers. Further, a PCR reaction can be performed according to a common method using a thermal cycler, Gene Amp PCR System 2400 manufactured by Applied Biosystems, with the use of TaqDNA polymerase (Takara Bio Inc.), KOD-Plus (Toyobo Co., Ltd.), etc.

A DNA of the present invention can be obtained by alteration of a nucleotide sequence, such alteration being a substitution, deletion, insertion or addition of amino acids at a specific site by means of, for example, site-directed mutagenesis. Further, an altered DNA such as the above can also be obtained by a conventionally known mutagenic treatment.

Still further, it is possible to obtain DNAs that encode substantially the same protein from general acetic acid bacteria, in particular, from species, strains, mutants or variants of the genus *Acetobacter* or the genus *Gluconacetobacter*, because it is generally known that an amino acid sequence of a protein and an nucleotide sequence encoding the same are slightly different among the species, strains, mutants or variants.

Specifically, a DNA encoding, for example, a protein which is substantially the same as a protein hybridizing under stringent conditions to a DNA which comprises a nucleotide sequence consisting of nucleotide numbers 1639 to 2268 or nucleotide numbers 849 to 1559 in the nucleotide sequence shown by SEQ ID NO: 1 (FIG. 2) in the sequence listing and which has the function as an acyl homoserine lactone synthase or an acyl homoserine lactone receptor-type transcription factor can be obtained by isolating the DNA encoding such protein from acetic acid bacteria belonging to the genus *Acetobacter* or the genus *Gluconacetobacter*, or mutated acetic acid bacteria belonging to the genus *Acetobacter* or the genus *Gluconacetobacter*, or from spontaneous mutants or variants thereof.

A mutant gene or homologous gene of the present invention consisting of a DNA encoding a protein consisting of an amino acid sequence wherein one or a few amino acids are substituted, deleted, inserted or added in the amino acid sequence shown by SEQ ID NO: 2 (FIG. 3) or SEQ ID NO: 3 (FIG. 4) in the sequence listing and having a growth-promoting function in the presence of acetic acid, or a DNA encoding a protein consisting of an amino acid sequence having at least 85% or more identity to the amino acid sequence shown by SEQ ID NO: 2 (FIG. 3) or SEQ ID NO: 3 (FIG. 4) in the sequence listing and having the activity of an acyl homoserine lactone synthase or the function as an acyl homoserine lactone receptor-type transcription factor, etc., can be isolated from other acetic acid bacteria or the like by screening a homologue of the above DNA under appropriate conditions with the use of a DNA fragment comprising the nucleotide sequence shown by SEQ ID NO: 1 (FIG. 2) in the sequence listing or a part thereof. The variant gene or homologous gene can also be prepared by a production method of an altered DNA as described above.

A DNA encoding a protein which is substantially the same as a protein hybridizing under stringent conditions to the nucleotide sequence shown by SEQ ID NO: 1 in the sequence listing or a probe prepared from a part thereof and having the function as an acyl homoserine lactone synthase and an acyl homoserine lactone receptor-type transcription factor can be obtained by isolating the above DNA from acetic acid bacteria belonging to the genus *Acetobacter* or the genus *Gluconacetobacter*, or mutated acetic acid bacteria belonging to the genus *Acetobacter* or the genus *Gluconacetobacter*, or from spontaneous mutants or variants thereof.

An acetic acid bacterium of the present invention is not particularly limited and is exemplified by a bacterium belonging to such as the genus *Acetobacter* or the genus *Gluconacetobacter* that have alcohol oxidation ability. An acetic acid bacterium of the present invention, however, is characterized in that it has been altered so that the function of a protein encoded by a gene involved in the quorum-sensing system has been reduced or deleted as described above. Examples of the acetic acid bacterium include the following.

Examples of the acetic acid bacterium belonging to the genus *Gluconacetobacter* include *Gluconacetobacter intermedius*, *Gluconacetobacter xylinus*, *Gluconacetobacter europaeus*, *Gluconacetobacter diazotrophicus* and *Gluconacetobacter entanii*, and more specifically include *Gluconacetobacter xylinus* IFO3288, *Gluconacetobacter europaeus* DSM6160, *Gluconacetobacter diazotrophicus* ATCC49037, *Acetobacter altoacetigenes* MH-24, and *Gluconacetobacter intermedius* NCI1051 (FERM BP-10767).

Further, examples of the acetic acid bacterium belonging to the genus *Acetobacter* include *Acetobacter aceti*, and more specifically include *Acetobacter aceti* No. 1023 and *Acetobacter aceti* IFO3283.

A method of the present invention for producing an acetic acid bacterium with enhanced acetic acid fermentation ability of an acetic acid bacterium by reducing or deleting the function of one or more proteins that are encoded by genes involved in the quorum-sensing system in acetic acid bacteria is exemplified by a method which comprises adding to a medium a substance which likely inhibits the expression of a gene involved in the quorum-sensing system in acetic acid bacteria or the activity of the protein encoded by the gene, and carrying out a culture. Examples of such substance include an antibacterial substance such as DHCP (4,5-dihydroxy-2-cyclopenten-1-one), and an acetic acid bacterium with enhanced acetic acid fermentation ability can be obtained by a culture preformed by adding an appropriate amount of the above antibacterial substance.

As a method for producing an acetic acid bacterium with enhanced acetic acid fermentation ability of the present invention, such method is also effective that reduces or deletes the function by modifying a gene involved in the quorum-sensing system in acetic acid bacteria. It is also effective to induce a mutation in a region of the gene where it is involved in the expression of the gene so as to inhibit the expression thereof. As a method to modify a gene, a method in which mutation is induced to the gene by a physical treatment or by using a chemical mutagenic agent is effective. As these methods for inducing mutation, methods conventionally practiced for acetic acid bacteria are effective. Examples of such conventional method include a method for inducing mutation by subjecting an acetic acid bacterium to an ultraviolet irradiation or treating an acetic acid bacterium with N-methyl-N'-nitro-N-nitrosoguanidine (NTG) or with a mutagenic agent usually used for mutagenic treatment such as nitrous acid.

Production of acyl homoserine lactone is thus decreased or ceased in a strain in which the function of an acyl homoserine lactone synthase is reduced or deleted by mutation. Further, since an acyl homoserine lactone receptor-type transcription factor activates transcription of a gene encoding an acyl homoserine lactone synthase, production of acyl homoserine lactone is also decreased or ceased in a strain in which the function as an acyl homoserine lactone receptor-type transcription factor is reduced or deleted.

Therefore, in order to select the acetic acid bacterium of the interest from acetic acid bacteria comprising mutagenesis, a strain in which production of acyl homoserine lactone is decreased or ceased may be selected. For example, a method for detecting acyl homoserine lactone by such as a bioassay can be employed. Specifically, a mutant strain is inoculated onto a medium which has been inoculated with a reporter strain producing a pigment in the presence of acyl homoserine lactone (see for example, Journal of Microbiological Methods, Vol. 44, pp. 239-251, 2001), and cultured. Subsequently, the pigment production amount in the reporter strain is confirmed and compared to that of the wild-type strain. Then, a mutant strain that does not induce the pigment production, that is, a mutant strain in which production of acyl homoserine lactone is decreased or ceased, may be selected.

Since acetic acid bacteria are known as bacteria that tend to mutate spontaneously, an acetic acid bacterium with enhanced acetic acid fermentation ability can also be obtained by isolating from the nature an acetic acid bacterium having a gene in which expression or function of the above enzymes has been spontaneously mutated. Such isolation of a spontaneous mutant strain can be practiced in a similar manner as for the above mutant strains by employing a method for detecting production of acyl homoserine lactone.

Further, since these genes have already been obtained and the nucleotide sequences thereof have also been elucidated, an acetic acid bacterium with enhanced acetic acid fermentation ability of the present invention can be produced by introducing a gene, which comprises mutagenesis by recombinating these genes, into the original acetic acid bacterium, then by reducing or deleting the function of the gene of the original acetic acid bacterium by employing such as a homologous recombination. For example, a method is effective wherein the method comprises transforming an acetic acid bacterium with a DNA comprising a gene that has been modified so as not to produce a normally functioning acyl homoserine lactone synthase by deleting a partial sequence of a gene encoding an acyl homoserine lactone synthase or by inserting a drug-resistant gene into the gene, and disrupting the normal gene on the chromosome in the transformed acetic acid bacterium by homologous recombination of the deleted or inserted gene. Similarly, an acetic acid bacterium with enhanced acetic acid fermentation ability, in which a gene of an acyl homoserine lactone receptor-type transcription factor is disrupted, can also be obtained.

In a bacterium strain, it is possible either to reduce or delete the function of one of the proteins encoded by genes involved in the quorum-sensing system of the present invention, or to reduce or delete the function of the two or more proteins. When suppressing the expression of the two or more proteins, a strain in which the function of one of the proteins encoded by the genes involved in the quorum-sensing system is reduced or deleted (called as a single-defected strain) is first produced by using the above-mentioned mutation or homologous recombination. An effective method then comprises: transforming the single-defected strain with a DNA comprising a gene which has been modified so as not to produce a normally functioning acyl homoserine lactone synthase such as by inserting a drug-resistant gene into the second gene that is involved in the quorum-sensing system; obtaining a transformant in which a normal second gene on the chromosome was disrupted by homologous recombination; and so on. If a drug-resistant gene is used for producing a single-defected strain, a different drug-resistant gene may be used in order to select transformants efficiently.

Transformation of an acetic acid bacterium may be conducted by such as a calcium chloride method (see for example, Agric. Biol. Chem., Vol. 49, p. 2091, 1985), and an electroporation method (see for example, Biosci. Biotech. Biochem., Vol. 58, p. 974, 1994).

As above, an acetic acid fermentation ability can be improved by altering an acetic acid bacterium belonging to the genus *Acetobacter* or the genus *Gluconacetobacter* having the alcohol oxidation ability in such away that the quorum-sensing system does not function normally by reducing or deleting the function of the quorum-sensing system as described above.

In addition, as a method of enhancing the acetic acid fermentation ability of an acetic acid bacterium by reducing or deleting the function of one or more proteins encoded by a gene that is involved in the quorum-sensing system in acetic acid bacteria, a method is exemplified in which an acetic acid bacterium is cultured under the physical conditions where the expression of a gene involved in the quorum-sensing system in the acetic acid bacterium or the activity of the protein encoded by the gene is inhibited. Examples of such conditions include culturing at a relatively low temperature.

A conventionally known method is employed for the method of producing vinegar of the present invention except that an acetic acid bacterium in which the function of the quorum-sensing system is reduced or deleted so that the quorum-sensing system does not function normally is cultured in an alcohol-containing medium, and the acetic acid is generated and accumulated in the medium. Namely, an acetic acid bacterium, in which the function of the quorum-sensing system is reduced or deleted to eliminate normal function of the quorum-sensing system, may be cultured basically under the conditions where acetic acid fermentation can be performed. Specifically, the culture may be conducted similarly to that in a production method of vinegar employing a conventional method for acetic acid fermentation.

As for an alcohol-containing medium, any medium suffices as long as it is a medium used for acetic acid fermentation. Those alcohol-containing media may be used that contain a carbon source, nitrogen source, inorganic substance, etc. other than an alcoholic component such as ethanol, and contain an appropriate amount of nutrient source required for growth of a bacterial strain in use, if necessary. A medium may be either a synthetic medium or a natural medium. Examples of the carbon source include various carbohydrates including glucose and sucrose, and various organic acids. As a nitrogen source, a natural nitrogen source such as peptone, degradation product of microbial cells or the like can be used.

Further, the culture is performed under an aerobic condition such as in a static culture, shaking culture, aeration-agitation culture and the like. The culture is performed at the temperature of 25 to 35° C., and usually at 30° C. The pH of medium is generally within the range of 2.5 to 7, preferably within the range of 2.7 to 6.5, and the pH can also be adjusted with various acids, various bases, buffers or the like. Generally, a 1- to 21-day culture can accumulate a high concentration of acetic acid in the medium.

A high acidity vinegar can be produced more efficiently by the above method for producing vinegar of the present invention. The present invention also relates to vinegar with reduced content of acyl homoserine lactone obtained by the method for producing vinegar of the present invention.

The present invention is specifically explained in the following with reference to the examples. The technical scope of the present invention, however, will not be limited to these exemplifications.

Example 1

Isolation of a Gene Encoding an Acyl Homoserine Lactone Synthase Derived from an Acetic Acid Bacterium In order to isolate a gene encoding an acyl homoserine lactone synthase of an acetic acid bacterium, *Gluconacetobacter intermedius* NCI1051 (hereinafter may be referred to as a wild-type strain) that was deposited under the Budapest Treaty under Accession Number: FERM BP-10767 on Jan. 31, 2007 with the International Patent Organism Depositary at the National Institute of Advanced Industrial Science and Technology (Central 6, 1-1 Higashi 1-Chome, Tsukuba-shi, Ibaraki-ken, Japan) was used to prepare a chromosomal DNA library of this wild-type strain.

Chromosomal DNA was extracted using GenomicPrep Cells and Tissue DNA Isolation Kit (Amersham Biosciences). The obtained chromosomal DNA was treated with the restriction enzyme Pst I (TAKARA BIO INC.) for 1 hour at 37° C.

Subsequently, the digested chromosomal DNA fragments were ligated to pUC19 to prepare recombinant DNAs.

Specifically, the restriction enzyme Pst I which was used for digesting the chromosomal DNA was allowed to act on a vector DNA for 1 hour or more at 37° C. to completely digest and cleave the vector DNA. Then, the chromosomal DNA fragments and the cleaved pUC19 were mixed, on which mixture the T4 DNA ligase was allowed to act for 6 hours at 16° C. to obtain the recombinant DNAs.

The obtained recombinant DNAs were transformed into *Escherichia coli* JM109 strain by electroporation method (see for example, Biosci. Biotech. Biochem., Vol. 58, p. 974, 1994).

Transformants are selected on a LB agar medium supplemented with 100 μg/ml antibiotic. Ampicillin-resistant transformants grown on the above selection medium were used as a chromosomal DNA library.

A fragment having a gene encoding an acyl homoserine lactone synthase was selected from this library according to the following method. Specifically, on an LB agar medium containing 500 μg/ml X-Gal which has been inoculated with *Agrobacterium tumefaciens* NTL4 (pZLR4) which is a reporter strain producing a pigment in the presence of acyl homoserine lactone (see for example, J. Bacteriol., Vol. 185, No. 19, pp. 5665-5672), strains from the chromosomal DNA library were inoculated adjacent to the reporter strain. After conducting a culture for 2 days at 30° C., a strain, which had induced a pigment production of the reporter strain was selected. A plasmid was recovered from thus selected strain and its nucleotide sequence was determined. As a result, the nucleotide sequence corresponding to the nucleotide numbers 1 to 2333 shown in FIG. 2 and by SEQ ID NO: 1 in the sequence listing was determined.

As a result, a DNA fragment was obtained that includes ORF (nucleotide numbers 1639 to 2268 shown in FIG. 2 and by SEQ ID NO: 1 in the sequence listing; hereinafter may be referred to as orf1) which encodes a protein (hereinafter may be referred to as Orf1) having only 21.2% identity to acyl homoserine lactone synthase from *Vibrio fischeri*.

Example 2

Preparation of a Strain Disrupted a Gene Encoding an Acyl Homoserine Lactone Synthase Primer 1 (see FIG. 5 and SEQ ID NO: 4 in the sequence listing) and primer 2 (see FIG. 6 and SEQ ID NO: 5 in the sequence listing) were synthesized based on the nucleotide sequence of orf1 obtained in Example 1, an upstream sequence and a 5'-side sequence of orf1 were amplified by PCR method using the chromosomal DNA of *Gluconacetobacter intermedius* NCI 1051 as a template, and the amplified product was treated with the restriction enzymes EcoRI and KpnI (TAKARA BIO INC.) to prepare a DNA fragment (DNA fragment 1).

Figure 8:
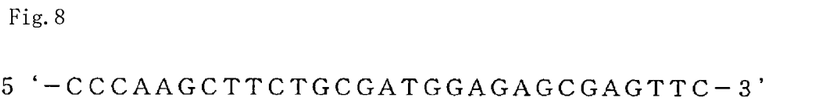
FIG. 8 shows the nucleotide sequence of primer 4 (SEQ ID NO: 7).

Similarly, primer 3 (see FIG. 7 and SEQ ID NO: 6 in the sequence listing) and primer 4 (see FIG. 8 and SEQ ID NO: 7 in the sequence listing) were synthesized, a 3'-side sequence and a downstream sequence of the orf1 structural gene were amplified by PCR method using the chromosomal DNA of *Gluconacetobacter intermedius* NCI 1051 as a template, and the amplified product was treated with the restriction enzyme Hind III (TAKARA BIO INC.) to prepare a DNA fragment (DNA fragment 2).

Figure 9:
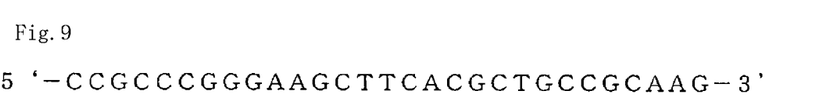
FIG. 9 shows the nucleotide sequence of primer 5 (SEQ ID NO: 8).
Figure 10:
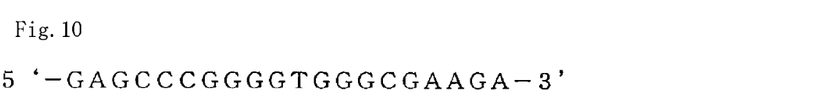
FIG. 10 shows the nucleotide sequence of primer 6 (SEQ ID NO: 9).

Further, a DNA fragment including a Kanamycin-resistant gene was amplified by PCR method using primer 5 (see FIG. 9 and SEQ ID NO: 8 in the sequence listing) and primer 6 (see FIG. 10 and SEQ ID NO: 9 in the sequence listing) with transposon Tn5 of *Escherichia coli* as a template, and the amplified product was treated with the restriction enzyme Sma I (TAKARA BIO INC.) to prepare a DNA fragment (DNA fragment 3).

The chromosomal DNA was extracted by using GenomicPrep Cells and Tissue DNA Isolation Kit (Amersham Bioscience). PCR reaction was conducted for 30 cycles with each cycle consisting of denaturation at 94° C. for 30 seconds, annealing at 55° C. for 30 seconds, and elongation at 72° C. for 1 minute, by using Pyrobest DNA Polymerase (TAKARA BIO INC.).

Subsequently, the DNA fragment 3 was ligated to the Sma I site in pUC18. Thus prepared DNA was transformed into *Escherichia coli* JM109 by electroporation method (see Biosci. Biotech. Biochem., Vol. 58, p. 974, 1994).

Transformants were selected on a LB agar medium supplemented with 100 μg/ml ampicillin. A plasmid DNA was prepared, according to a common method, from the ampicillin-resistant transformant grown on the above selection medium. The DNA fragment 1 was linked to EcoRI-kpnI site and the DNA fragment 2 was similarly linked to Hind III site of thus obtained plasmid DNA to transform *Escherichia coli*, and the plasmid pUCΔorf1 for disrupting orf1 was prepared.

*Gluconacetobacter intermedius* NCI 1051 (hereinafter may be referred to as wild-type strain) was transformed by electroporation method (Proc. Natl. Acad. Sci. U.S.A., Vol. 87, pp. 8130-8134, 1990) by using thus obtained plasmid pUCΔorf1 for disrupting orf1.

Transformants were selected on a YPG medium (3% glucose, 0.5% yeast extract and 0.3% polypeptone) supplemented with 100 μg/ml kanamycin. A chromosomal DNA was extracted from the kanamycin-resistant transformant grown on the selection medium, and it was confirmed by southern hybridization that the kanamycin-resistant gene was inserted in orf1 gene and the orf1 gene was disrupted.

Thus obtained transformant, *Gluconacetobacter intermedius* NCI 1051Δorf1 (hereinafter may be referred to as the orf1-disrupted strain) was deposited under the Budapest Treaty on Jan. 31, 2007 with the International Patent Organism Depositary at the National Institute of Advanced Industrial Science and Technology (Central 6, 1-1 Higashi 1-Chome, Tsukuba-shi, Ibaraki-ken), and the Accession Number is FERM BP-10768.

Example 3

Functional Analysis of Orf1

The activity of an acyl homoserine lactone synthase in a wild-type strain and the orf1-disrupted gene was determined. The activity of an acyl homoserine lactone synthase was detected by bioassay method (see for example, J. Bacteriol., Vol. 188, No. 5, pp. 1943-1949, 2006).

First, a wild-type strain and the orf1-disrupted strain were cultured in a YPG medium containing 2% ethanol and 1% Celluclast 1.5 L (Novozymes), and samples of culture broths were taken intermittently. These culture broths were filtered with a 0.22 μm filter to obtain supernatants, respectively. To each supernatant, an equal amount of ethyl acetate was added and stirred well, and the ethyl acetate fraction was recovered. An equal amount of ethyl acetate was added again to the aqueous fraction and the ethyl acetate fraction was recovered.

The ethyl acetate fractions thus obtained were put together and ethyl acetate was removed by a centrifugal evaporator. Thus generated precipitation was dissolved in dimethylsulfoxide to prepare a sample for bioassay.

Then, *Agrobacterium tumefaciens* NTL4 (pZLR4) (see for example, J. Bacteriol., Vol. 185, No. 19, pp. 5665-5672), which is a reporter strain for detecting acyl homoserine lactone, was cultured for 12 hours at 30° C. in the medium A (0.2% glucose, 0.1% yeast extract, 0.3% dipotassium hydrogen phosphate, 0.1% sodium dihydrogen phosphate, 0.1% ammonium chloride, 0.03% magnesium sulfate heptahydrate, 0.015% potassium chloride, 0.001% calcium chloride dihydrate, 0.00025% ferrous sulfate heptahydrate and 5 μg/μl gentamicin), to prepare a preculture. To the medium A that had been inoculated with the preculture, a bioassay sample prepared from the above supernatant was added and cultured for 6 hours at 30° C.

Thus prepared culture broth was measured for its β-galactosidase activity. The β-galactosidase activity was measured according to a common method (see for example, Molecular Cloning, 2nd Ed., p. 17.35, 1989).

As above, the acyl homoserine lactone concentrations in culture broths of the wild-type and orf1-disrupted strains were examined. The results are shown in FIG. 1.

Figure 1:
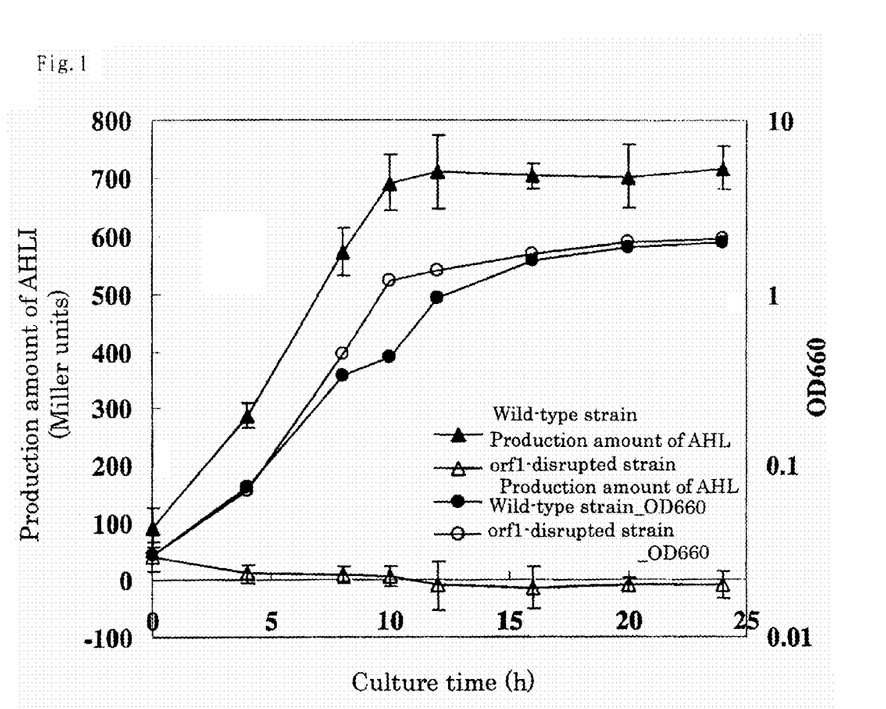
FIG. 1 shows concentration of acyl homoserine lactone (AHL) and growth (OD660) in a culture broth of a strain in which an acyl homoserine lactone synthase gene has been disrupted.

As is clear from FIG. 1, acyl homoserine lactone was detected in the wild-type strain but not in the orf1-disrupted strain. This result confirmed that the Orf1 protein encoded by orf1 is an acyl homoserine lactone synthase.

Example 4

Acetic Acid Fermentation Test for the orf1-Disrupted Strain

The orf1-disrupted strain obtained in Example 2 whose orf1 gene had been disrupted was compared to a wild-type strain for the acetic acid fermentation ability. Specifically, an aeration-agitation culture was carried out at 30° C., 500 rpm and 1 L/min in a medium (1.5 L) containing 3% ethanol, 3% glucose, 0.5% yeast extract, 0.3% polypeptone, 100 µg/ml ampicillin, 1% Celluclast 1.5 L (Novozymes) and 0.01% defoaming agent by using a 3-liter mini-jar (Bioneer 300, 3 L; B.E. MARUBISHI Co. Ltd.). The ethanol concentration in the medium was controlled at 2% during fermentation. Fermentation results are shown in Table 1.

TABLE 1

|  | Wild-type strain | orf1-disrupted strain |
|---|---|---|
| Production rate (%/hr) | 0.117 | 0.178 |
| Acetic acid concentration (%) | 3.30 | 4.68 |

As is clear from Table 1, it was demonstrated that the average production rate during the 24-hour culture of the orf1-disrupted strain is about 1.5-fold higher than that of the wild-type strain, and that the fermentation time can be reduced. Further, the acetic acid concentration in the culture broth was 4.68% for the orf1-disrupted strain as compared to 3.30% for the wild-type strain, which was an increase by about 1.4-fold. It was thus demonstrated that the orf1-disrupted strain enables a more efficient production of vinegar containing a higher concentration of acetic acid.

This result indicated that the acetic acid fermentation ability of an acetic acid bacterium is enhanced by disrupting orf1 which encodes an acyl homoserine lactone synthase, and that vinegar containing a high concentration of acetic acid can be produced more efficiently.

Example 5

Isolation of a Gene Encoding an Acyl Homoserine Lactone Receptor-Type Transcription Factor Derived from an Acetic Acid Bacterium As a result of determining the nucleotide sequence of the DNA fragment obtained in Example 1, a DNA fragment was obtained, which contains ORF (nucleotide numbers 849-1559 shown in FIG. 2 and by SEQ ID NO: 1 in the sequence listing; hereinafter may be referred to as orf2) that encodes a protein (hereinafter may be referred to as Orf2) having only 26.2% identity to the acyl homoserine lactone receptor-type transcription factor of *Vibrio fischeri*, in the upstream of the gene encoding an acyl homoserine lactone synthase.

Example 6

Figure 11:
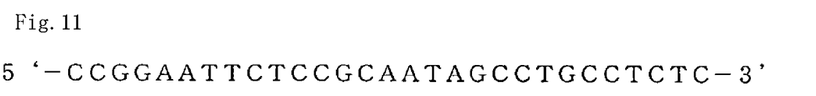
FIG. 11 shows the nucleotide sequence of primer 7 (SEQ ID NO: 10).
Figure 12:
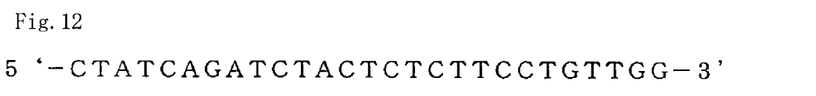
FIG. 12 shows the nucleotide sequence of primer 8 (SEQ ID NO: 11).

Preparation of a Strain Disrupted a Gene Encoding an Acyl Homoserine Lactone Receptor-Type Transcription Factor Primer 7 (see FIG. 11 and SEQ ID NO: 10 in the sequence listing) and primer 8 (see FIG. 12 and SEQ ID NO: 11 in the sequence listing) were synthesized based on the nucleotide sequence of orf2 obtained in Example 5, a sequence including orf2 was amplified by PCR method using the chromosomal DNA of *Gluconacetobacter intermedius* NCI 1051 as a template, and the amplified product was treated with the restriction enzymes EcoRI and SmaI (TAKARA BIO INC.) to prepare a DNA fragment (DNA fragment 4).

Further, a DNA fragment that includes a Kanamycin-resistant gene was amplified by PCR method using primer 5 (see FIG. 9 and SEQ ID NO: 8 in the sequence listing) and primer 6 (see FIG. 10 and SEQ ID NO: 9 in the sequence listing) with transposon Tn5 of *Escherichia coli* as a template, and the amplified product was treated with the restriction enzyme Sma I (TAKARA BIO INC.) to prepare a DNA fragment (DNA fragment 5).

The chromosomal DNA was extracted by using GenomicPrep Cells and Tissue DNA Isolation Kit (Amersham Bioscience). PCR reaction was conducted for 30 cycles with each cycle consisting of denaturation at 94° C. for 30 seconds, annealing at 55° C. for 30 seconds, and elongation at 72° C. for 1 minute, by using Pyrobest DNA Polymerase (TAKARA BIO INC.).

Subsequently, the PCR product 4 was linked to the EcoRI and SmaI sites in pUC19. Thus prepared DNA was transformed into *Escherichia coli* JM109 by electroporation method (see for example, Biosci. Biotech. Biochem., Vol. 58, p. 974, 1994). Transformants were selected on a LB agar medium supplemented with 100 µg/ml ampicillin. A plasmid DNA was prepared according to a common method from the ampicillin-resistant transformant grown on the above selection medium. This plasmid was treated with EcoR V (TAKARA BIO INC.) for digestion within orf2, and the DNA fragment 5 was ligated thereto.

*Escherichia coli* was transformed as above with thus prepared DNA, and a plasmid DNA was prepared by a common method to obtain the plasmid pUCΔorf2 for disrupting orf2.

A wild-type strain was transformed with thus obtained plasmid pUCΔorf2 for disrupting orf2 by electroporation method (see for example, Proc. Natl. Acad. Sci. U.S.A., Vol. 87, pp. 8130-8134, 1990).

Transformants were selected on a YPG medium (3% glucose, 0.5% yeast extract and 0.3% polypeptone) supplemented with 100 µg/ml kanamycin. A chromosomal DNA was extracted from the kanamycin-resistant transformant grown on the selection medium, and it was confirmed by southern hybridization that the kanamycin-resistant gene was inserted in the orf2 gene and the orf2 gene was disrupted.

Thus obtained transformant, *Gluconacetobacter intermedius* NCI 1051Δorf2 (hereinafter may be referred to as the orf2-disrupted strain) was deposited under the Budapest Treaty on Jan. 31, 2007 with the International Patent Organism Depositary at the National Institute of Advanced Industrial Science and Technology (Central 6, 1-1 Higashi 1-Chome, Tsukuba-shi, Ibaraki-ken), and the Accession Number is FERM BP-10769.

Example 7

Functional Analysis of Orf2

An acyl homoserine lactone receptor-type transcription factor forms a complex with acyl homoserine lactone and controls transcription of the specific genes. One example of the genes that are controlled by a complex of an acyl homoserine lactone receptor-type transcription factor and an acyl homoserine lactone is a gene encoding an acyl homoserine lactone synthase. Such complex had been known to bind to the upstream of this gene to activate its transcription (see for example, J. Bacteriol., Vol. 185, No. 19, pp. 5665-5672, 2004). Therefore, the present inventor performed functional presumption by a motif search of proteins, assay of DNA-binding ability by a gel shift assay, and transcriptional analysis of orf1, and extrapolated that Orf2 is an acyl homoserine lactone receptor-type transcription factor.

By a motif search using the NCBI domain search (http://www.ncbi.nlm.nih.gov/structure/cdd/cdd.shtml), the acyl homoserine lactone receptor domain (pfam03472.10) was found to be present on the N-terminal side and the helix-turn-helix DNA binding motif (Smart00421.11) was found to be present on the C-terminal side of Orf2.

Next, a gel shift assay was carried out according to the method of Urbanowski et al. (see for example, J. Bacteriol., Vol. 185, No. 19, pp. 5665-5672, 2004). The Orf2 protein highly expressed in *Escherichia coli* was used, and an upstream sequence (nucleotides 1349-1749 in SEQ ID NO: 1 in the sequence listing) of orf1 gene was used as a probe. As a result, it was suggested that Orf2 binds to the upstream of orf1 gene in the presence of acyl homoserine lactone.

Further, RNA was extracted from the wild-type strain and orf2-disrupted strain, and the transcriptional analysis of orf1 was performed by Northern hybridization.

RNA was extracted by a hot phenol method from bacterial cells that had been cultured for 8 hours in a YPG medium containing 2% ethanol and 1% Celluclast 1.5 L (Novozymes). As a result, transcription of orf1 was observed in the wild-type strain but not in the orf2-disrupted strain.

Above results confirmed that Orf2 functions as an acyl homoserine lactone receptor-type transcription factor.

Example 8

Acetic Acid Fermentation Test for *Gluconacetobacter intermedius* NCI1051Δorf2

The orf2-disrupted strain obtained in Example 3 was compared to a wild-type strain for the acetic acid fermentation ability. Specifically, an aeration-agitation culture was carried out at 30° C., 500 rpm and 1.0 L/min in a medium (1.5 L) containing 3% ethanol, 3% glucose, 0.5% yeast extract, 0.3% polypeptone, 100 µg/ml ampicillin, 1% Celluclast 1.5 L (Novozymes) and 0.01% defoaming agent by using a 3-liter mini-jar (Bioneer 300, 3 L; B.E. MARUBISHI Co. Ltd.). The ethanol concentration in the medium was controlled at 2% during fermentation. Fermentation results are shown in Table 2.

TABLE 2

|  | Wild-type strain | orf2-disrupted strain |
|---|---|---|
| Production rate (%/hr) | 0.117 | 0.183 |
| Acetic acid concentration (%) | 3.30 | 4.68 |

As is clear from Table 2, it was demonstrated that the average production rate during the 24-hour culture of the orf2-disrupted strain is about 1.4-fold higher than that of the wild-type strain, and also that the fermentation time can be reduced. Further, the acetic acid concentration in the culture broth was 4.68% for the orf2-disrupted strain as compared to 3.30% for the wild-type strain, which was an increase by about 1.6-fold. It was thus demonstrated that the transformant is applicable to production of vinegar containing a higher concentration of acetic acid.

This result indicated that the acetic acid fermentation ability of an acetic acid bacterium is enhanced by disrupting orf2 which encodes an acyl homoserine lactone receptor-type transcription factor, and that vinegar containing a high concentration of acetic acid can be produced more efficiently.

INDUSTRIAL APPLICABILITY

According to the present invention, genes involved in the quorum-sensing system in acetic acid bacteria and the proteins encoded by the genes are provided. Further provided is a method to remarkably enhance the acetic acid fermentation ability of acetic acid bacteria by reducing or deleting the function of proteins encoded by the genes involved in the quorum-sensing system in acetic acid bacteria, and the method enables more efficient production of vinegar containing a high concentration of acetic acid by using the acetic acid bacteria.

The invention claimed is:

1. A method for enhancing the acetic acid fermentation ability of an acetic acid bacterium belonging to the genus *Acetobacter* or the genus *Gluconacetobacter*, wherein the function of one or two proteins which are encoded by the genes involved in the quorum-sensing system in the acetic acid bacterium belonging to the genus *Acetobacter* or the genus *Gluconacetobacter* is reduced or deleted,
   wherein the gene involved in the quorum-sensing system is a gene encoding:
   (A) a protein consisting of the amino acid sequence of SEQ ID NO: 2; or
   (B) a protein which consists of an amino acid sequence having at least 90% or more identity to the amino acid sequence of SEQ ID NO: 2, and which has the activity of an acyl homoserine lactone synthase,
   or a gene encoding:
   (A) a protein consisting of the amino acid sequence of SEQ ID NO: 3; or
   (B) a protein which consists of an amino acid sequence having at least 90% or more identity to the amino acid sequence of SEQ ID NO: 3, and which has the function as an acyl homoserine lactone receptor-type transcription factor.

2. The method of claim 1, wherein the protein consists of an amino acid sequence having at least 95% or more identity to the amino acid sequence of SEQ ID NO: 2 or having at least 95% or more identity to the amino acid sequence of SEQ ID NO: 3.

3. The method of claim 1, wherein the protein consists of an amino acid sequence having at least 96% or more identity to the amino acid sequence of SEQ ID NO: 2 or having at least 96% or more identity to the amino acid sequence of SEQ ID NO: 3.

4. The method of claim 1, wherein the protein consists of an amino acid sequence having at least 98% or more identity to the amino acid sequence of SEQ ID NO: 2 or having at least 98% or more identity to the amino acid sequence of SEQ ID NO: 3.

5. The method of claim 1, wherein the protein consists of an amino acid sequence having at least 99% or more identity to the amino acid sequence of SEQ ID NO: 2 or having at least 99% or more identity to the amino acid sequence of SEQ ID NO: 3.

* * * * *

SEQUENCE LISTING

```
<160> NUMBER OF SEQ ID NOS: 11

<210> SEQ ID NO 1
<211> LENGTH: 2333
<212> TYPE: DNA
<213> ORGANISM: Gluconacetobacter intermedius

<400> SEQUENCE: 1
ctgcagccag cgtcatcggc ttggttgcta ttgtcctgaa cggtttattt aaagtcaaaa      60
aagaagaaga aaaagctaaa gaaaaagaag gcgataataa gtcagcctag atagccacca     120
ctgcgacaat gcgcgaacgg aaatagcttt aagggcgtct cggaaatcat gcgcctaacc     180
accctcgccc tactcaccac cccagcagca gctcacgcct acgcaccccg gcacgcctat     240
acgccaacca gcggccaagc tgagccagtc tgccccaagg gcgaccagcc ggtttgggtg     300
aacacccggt ctagcgtcta ccactaccgg cacgaacgct ggtacgggaa cacaaaatat     360
gggcagtatg agtgtgagaa ggacgcgcag gccgagggga acaggcctac gcggaatggc     420
cagtaagaac ggtcagaacg ggttttctac gttatccgcg ggtttcgcgt catcaacctg     480
```

```
agccttgatg ctatgagagg catctgtggg tgtggtcttc cgtagattac gtgacttatg    540
gcgcacgcct cgaacgcctg acttcttgtc ccccttccg caatagcctg cctctcgcat     600
tcatagacgc cgtgtttggt tcggccatac cagcgatcgc ccggcagatg atagacgcca    660
gtgttctggt tgacccagac catggtatca gcagggcatg atgggtgggg cagattttcg    720
gctgcgtagg ctgctcccgg catgaggacg gcgatcgcca ccataaatct atagaataaa    780
tatatcatat aatttaggct tattattgaa tgcactggag gtagatgcgg catagatggt    840
gggcttgacg attgaccttc tggcgaaact catgaccttg agaacgcag ccactaaaca     900 cgatctgcta tccatctatc ttgatgccgt cctgtcagtc gggaacgtcc acgtaaccat    960
tgtggaattg aacaggattg aagaccctaa agaaaatttt atacacgttg atatccgac    1020 ggaatgggtc aatttctata ttgagaacaa ttacatagtc tctgacccaa taataaaaaa   1080
atccagattc atgagccacc catatttctg gcatgaaatc aagaacatca acaaagccga   1140 aaaaagata  atcaggacg  tatctgaatt tggcataaaa aaggggctga caataccggt    1200
ccatacgcat gacagggtaa tttacgccat ttgttttgca tttacagata aaaacataga   1260
tcgggaaatt gagcttatt  tgcgcgcctt atccaatttc ttcattaccg gttataaaaa   1320
attggatgaa ccggcggata tgtcgctccc cattcttacc cctcgtgaaa agaatgcct    1380 gacatggaca gccaagggca aaagctcatg ggaaacggg  atgattgttg gtgtcagtga   1440
gcgcacagtt aactttcaca tcaacaatgc cttgctgaag ctgaaatgta cgaatcgtat   1500
catgggtgtg gtgcgggcta tctgcgcagg gctgattgaa ctgtaaaacc tgtcaggtct   1560
gacaggtaac ctgaccgtcg attttcatga atgatcctct catccaacag gaagagagta   1620
gatccatgat cgaagtcgta accgttgaaa acgcccactg ggccggaact gctctcgcag   1680
agcagttcaa gttccgttac cgccattttg tggctaatga gcagtgggaa gtccccttct   1740
acaagggcat ggaatacgat cagttcgata cgcctgctgc tgtctacctc gtgtggcgcg   1800
atgttgcggg cgttgttcgg ggcatgatcc gtctgctgcc aacgaaccgg ccttacatgc   1860
tggaaacact ctggcccgat atgatgcccg atccgattgt tccatctggt cctgcggtct   1920
gggaaatcac ccggtttggc gttgagcgca atctgtccct atccctccgc aagcagatat   1980
cagccgaact gatcctggca tgcatcgaat tttcagtgct gaatgacatt cacacctatc   2040
tgtttctgac agcgtggggt gttctcaagc ggattgtgcc cggcgctggc gtggaggcac   2100
agattcacag caggaagaca ctgccttccg gacatgatgt cgcttctgcc gttgtgcccg   2160
tttcccaggc cgttctggat aaggcccgag ccaagctgaa tattcattac gccgttctcg   2220
ataacaatag cattgagcag cagcatgcag cataggcagc agaacgaaga catggaaaaa   2280
aaagcagaaa acatcaaaag cgcattatcg ttcttgcggt cagaagcaag aaa          2333
```

<210> SEQ ID NO 2
<211> LENGTH: 222
<212> TYPE: PRT
<213> ORGANISM: Gluconacetobacter intermedius

<400> SEQUENCE: 2

```
Met Asn Asp Pro Leu Ile Gln Gln Glu Glu Ser Arg Ser Met Ile Glu
1               5                   10                  15

Val Val Thr Val Glu Asn Ala His Trp Ala Gly Thr Ala Leu Ala Glu
                20                  25                  30

Gln Phe Lys Phe Arg Tyr Arg His Phe Val Ala Asn Glu Gln Trp Glu
            35                  40                  45
```

```
Val Pro Phe Tyr Lys Gly Met Glu Tyr Asp Gln Phe Asp Thr Pro Ala
    50                  55                  60

Ala Val Tyr Leu Val Trp Arg Asp Val Ala Gly Val Arg Gly Met
65                  70                  75                  80

Ile Arg Leu Leu Pro Thr Asn Arg Pro Tyr Met Leu Glu Thr Leu Trp
                    85                  90                  95

Pro Asp Met Met Pro Asp Pro Ile Val Pro Ser Gly Pro Ala Val Trp
                100                 105                 110

Glu Ile Thr Arg Phe Gly Val Glu Arg Asn Leu Ser Leu Ser Leu Arg
                115                 120                 125

Lys Gln Ile Ser Ala Glu Leu Ile Leu Ala Cys Ile Glu Phe Ser Val
    130                 135                 140

Leu Asn Asp Ile His Thr Tyr Leu Phe Leu Thr Ala Trp Gly Val Leu
145                 150                 155                 160

Lys Arg Ile Val Pro Gly Ala Gly Val Glu Ala Gln Ile His Ser Arg
                165                 170                 175

Lys Thr Leu Pro Ser Gly His Asp Val Ala Ser Ala Val Val Pro Val
                180                 185                 190

Ser Gln Ala Val Leu Asp Lys Ala Arg Ala Lys Leu Asn Ile His Tyr
    195                 200                 205

Ala Val Leu Asp Asn Asn Ser Ile Glu Gln Gln His Ala Ala
    210                 215                 220

<210> SEQ ID NO 3
<211> LENGTH: 236
<212> TYPE: PRT
<213> ORGANISM: Gluconacetobacter intermedius
<220> FEATURE:
<221> NAME/KEY: MISC_FEATURE
<222> LOCATION: (186)..(186)
<223> OTHER INFORMATION: X stands for any amino acid
<220> FEATURE:
<221> NAME/KEY: MISC_FEATURE
<222> LOCATION: (203)..(203)
<223> OTHER INFORMATION: X stands for any amino acid

<400> SEQUENCE: 3

Met Val Gly Leu Thr Ile Asp Leu Leu Ala Lys Leu His Asp Leu Glu
1               5                   10                  15

Asn Ala Ala Thr Lys His Asp Leu Leu Ser Ile Tyr Leu Asp Ala Val
                20                  25                  30

Leu Ser Val Gly Asn Val His Val Thr Ile Val Glu Leu Asn Arg Ile
            35                  40                  45

Glu Asp Pro Lys Glu Asn Phe Ile His Val Gly Tyr Pro Thr Glu Trp
    50                  55                  60

Val Asn Phe Tyr Ile Glu Asn Asn Tyr Ile Val Ser Asp Pro Ile Ile
65                  70                  75                  80

Lys Lys Ser Arg Phe Met Ser His Pro Tyr Phe Trp His Glu Ile Lys
                85                  90                  95

Asn Ile Asn Lys Ala Glu Lys Lys Ile Ile Arg Asp Val Ser Glu Phe
                100                 105                 110

Gly Ile Lys Lys Gly Leu Thr Ile Pro Val His Thr His Asp Arg Val
            115                 120                 125

Ile Tyr Ala Ile Cys Phe Ala Phe Thr Asp Lys Asn Ile Asp Arg Glu
    130                 135                 140

Ile Glu Leu Tyr Leu Arg Ala Leu Ser Asn Phe Phe Ile Thr Gly Tyr
145                 150                 155                 160

Lys Lys Leu Asp Glu Pro Ala Asp Met Ser Leu Pro Ile Leu Thr Pro
```

```
                        165                 170                 175
Arg Glu Lys Glu Cys Leu Thr Trp Thr Xaa Lys Gly Lys Ser Ser Trp
            180                 185                 190

Glu Thr Gly Met Ile Val Gly Val Ser Glu Xaa Thr Val Asn Phe His
        195                 200                 205

Ile Asn Asn Ala Leu Leu Lys Leu Lys Cys Thr Asn Arg Ile Met Gly
    210                 215                 220

Val Val Arg Ala Ile Cys Ala Gly Leu Ile Glu Leu
225                 230                 235

<210> SEQ ID NO 4
<211> LENGTH: 29
<212> TYPE: DNA
<213> ORGANISM: Artificial
<220> FEATURE:
<223> OTHER INFORMATION: Primer 1

<400> SEQUENCE: 4
ccggaattcg gatatgtcgc tccccattc                                    29

<210> SEQ ID NO 5
<211> LENGTH: 29
<212> TYPE: DNA
<213> ORGANISM: Artificial
<220> FEATURE:
<223> OTHER INFORMATION: Primer 2

<400> SEQUENCE: 5
cggggtaccg ccagagtgtt tccagcatg                                    29

<210> SEQ ID NO 6
<211> LENGTH: 29
<212> TYPE: DNA
<213> ORGANISM: Artificial
<220> FEATURE:
<223> OTHER INFORMATION: Primer 3

<400> SEQUENCE: 6
cccaagcttc cgatatgatg cccgatccg                                    29

<210> SEQ ID NO 7
<211> LENGTH: 29
<212> TYPE: DNA
<213> ORGANISM: Artificial
<220> FEATURE:
<223> OTHER INFORMATION: Primer 4

<400> SEQUENCE: 7
cccaagcttc tgcgatggag agcgagttc                                    29

<210> SEQ ID NO 8
<211> LENGTH: 29
<212> TYPE: DNA
<213> ORGANISM: Artificial
<220> FEATURE:
<223> OTHER INFORMATION: Primer 5

<400> SEQUENCE: 8
ccgcccggga agcttcacgc tgccgcaag                                    29

<210> SEQ ID NO 9
<211> LENGTH: 20
<212> TYPE: DNA
<213> ORGANISM: Artificial
<220> FEATURE:
```

```
<223> OTHER INFORMATION: Primer 6

<400> SEQUENCE: 9
gagcccgggg tgggcgaaga                                               20

<210> SEQ ID NO 10
<211> LENGTH: 29
<212> TYPE: DNA
<213> ORGANISM: Artificial
<220> FEATURE:
<223> OTHER INFORMATION: Primer 7

<400> SEQUENCE: 10
ccggaattct ccgcaatagc ctgcctctc                                     29

<210> SEQ ID NO 11
<211> LENGTH: 27
<212> TYPE: DNA
<213> ORGANISM: Artificial
<220> FEATURE:
<223> OTHER INFORMATION: Primer 8

<400> SEQUENCE: 11
ctatcagatc tactctcttc ctgttgg                                       27
```